United States Patent [19]

Cihonski

[11] 4,300,010
[45] Nov. 10, 1981

[54] PRODUCTION OF ETHYLBENZENE

[75] Inventor: John L. Cihonski, Odessa, Tex.

[73] Assignee: El Paso Products Company, Odessa, Tex.

[21] Appl. No.: 144,887

[22] Filed: Apr. 29, 1980

[51] Int. Cl.$^3$ .......................... C07C 5/41; C07C 85/11
[52] U.S. Cl. .................................... 585/434; 564/423
[58] Field of Search ................ 564/416, 423; 585/434, 585/445

[56] References Cited

U.S. PATENT DOCUMENTS

| 1,845,280 | 2/1932 | Jaeger | 564/416 X |
| 3,253,038 | 5/1966 | Wise | 564/416 |
| 3,376,215 | 4/1968 | Bertolacini et al. | 585/434 X |
| 3,427,355 | 2/1969 | Le Maistre et al. | 564/416 |
| 3,502,736 | 3/1970 | Sato et al. | 585/434 X |
| 3,903,185 | 9/1975 | Vogel et al. | 585/434 X |
| 4,163,761 | 8/1979 | Patterson et al. | 585/445 X |
| 4,210,603 | 7/1980 | Cihonski | 564/423 X |

*Primary Examiner*—Robert V. Hines
*Attorney, Agent, or Firm*—Depaoli & O'Brien

[57] ABSTRACT

This invention provides a process for selective conversion of vinylcyclohexene to ethylbenzene in the presence of a palladium on nonacidic zeolite catalyst.

In the catalyst preparation, the catalyst is calcined first in air and then in a hydrocarbon type environment. Without the two step calcination procedure, the catalyst has a lower level of activity and selectivity.

7 Claims, No Drawings

PRODUCTION OF ETHYLBENZENE

BACKGROUND OF THE INVENTION

The importance of styrene as a large volume organic commodity has stimulated increasing efforts to develop new and improved methods for efficient synthesis of the compound.

In many of the processes contemplated for styrene synthesis, vinylcyclohexene or ethylbenzene function as starting materials or as key intermediates.

U.S. Pat. No. 2,976,331 describes a method for simultaneously effecting the catalytic dehydrogenation of a naphthenic hydrocarbon to an aromatic and the catalytic hydrogenation of an olefin to paraffins which involves contacting a naphthene/olefin mixture at 350°–850° F. with a crystalline metallo-alumino-silicate catalyst having uniform pores of 10–13 angstroms.

U.S. Pat. No. 3,502,736 describes a method for the oxidative dehydrogenation of a nonaromatic cyclic hydrocarbon having at least one unsaturated bond in a side chain, which method consists of contacting the said cyclic hydrocarbon in the presence of oxygen with a catalyst consisting of palladium oxyhydrate. In Example 1, the conversion rate of vinylcyclohexene is 86.8 percent, and the selectivity to styrene is 91.3 percent.

U.S. Pat. No. 3,903,185 describes a dehydrogenation process which is reported to be capable of converting vinylcyclohexene to ethylbenzene with a 96.6 percent selectivity. The process parameters include a 350°–450° C. temperature, a 2.5–30 atmospheres pressure, 0.2–20 m$^3$ of hydrogen/kg of vinylcyclohexene, and a catalyst containing metal elements selected from subgroups VI–VIII of the periodic table.

U.S. Pat. No. 4,163,761 describes a liquid phase process which involves converting vinylcyclohexene to styrene at a temperature of 170°–360° C. in the presence of a nitro compound and a copper chromite catalyst. The Example 1 data indicate a 19.2 percent selectivity of vinylcyclohexene to styrene, and a 7.5 percent selectivity to ethylbenzene.

U.S. Pat. No. 4,165,441 describes a vapor phase process for converting vinylcyclohexene to styrene which involves contacting vinylcyclohexene with oxygen in the presence of a tin-antimony oxide catalyst. A typical result in Table 1 indicates 82.4 percent vinylcyclohexene conversion, and a product selectivity of 58.9 percent styrene and 6 percent ethylbenzene, respectively.

Other United States patents of general interest with respect to dehydrogenation technology include U.S. Pat. Nos. 2,392,960; 2,404,104; 2,438,041; 2,560,329; 3,236,903; 3,409,690; 3,437,703; 3,511,885; and references cited therein.

The prior art vinylcyclohexene dehydrogenation processes characteristically produce mixtures of styrene and ethylbenzene, and usually only partial conversions are achieved. In many cases good conversion rates are counterbalanced by short-lived catalyst activity. Further, high temperatures and pressures cause cracking and isomerization side reactions. Objectional amounts of benzene, toluene and xylene are formed, and these are difficult to separate from ethylbenzene. Some processes require the use of hydrogen, which adversely affects the economics of a process.

Accordingly, it is an object of this invention to provide a process which is adapted to convert vinylcyclohexene to ethylbenzene under relatively mild conditions with a conversion of at least 90 percent and a selectivity of at least 95 percent.

It is a further object of this invention to provide a dehydrogenation catalyst which exhibits long term activity under continuous operating conditions, and which is highly selective for vinylcyclohexene conversion to ethylbenzene.

Other objects and advantages of the present invention shall become apparent from the accompanying description and examples.

DESCRIPTION OF THE INVENTION

One or more objects of the present invention are accomplished by the provision of a process for converting vinylcyclohexene to ethylbenzene with a conversion of at least about 90 percent and a selectivity of at least about 95 percent, which comprises contacting the vinylcyclohexene with molecular oxygen at a temperature in the range between about 190°–260° C. in the presence of a catalyst consisting essentially of palladium supported on a non-acidic zeolite carrier substrate; wherein the said catalyst has been pretreated by calcination in a molecular oxygen-containing atmosphere and then by calcination in a hydrogen or $C_1$–$C_{10}$ nonaromatic hydrocarbon-containing atmosphere prior to vinylcyclohexene conversion.

The term "vinylcyclohexene" refers to a feedstock which contains a substantial proportion of 4-vinylcyclohexene-1 (e.g., butadiene dimer as illustrated in U.S. Pat. No. 2,544,808). The feed material may include components such as propane or benzene which are non-reactive under the process conditions; and may include components which are reactive under the process conditions such as n-butane, isobutane, n-butenes, isobutylene, butadiene, n-octenes, 2-vinylcyclohexene, 3-vinylcyclohexene, ethylcyclohexane, and the like.

In reference to the catalyst composition employed in the process, the term "non-acidic" zeolite is meant to include alkali metal and alkaline earth metal forms of zeolites having a pore size liess than about 5 angstrom units (5 A) as a preferred type of carrier substrate component.

Assuming in zeolites one equivalent per aluminum atom, the equivalent ratio of alkali or alkaline earth metal to aluminum is nominally 1±0.05. This corresponds to 95 percent or more protonic sites (H+) which are substituted by atoms selected from alkali and alkaline earth metal cations such as Na+, K+, Ca++, Mg++, and the like.

Illustrative of non-acidic zeolite substrates suitable for the practice of the present invention vinylcyclohexene conversion process are alkali metal and alkaline earth metal forms of various natural and synthetic crystalline aluminosilicates known in the prior art, such as zeolite A, analcime, chabazite, gmelinite, harmotome, levynite, mordenite, and the like.

The preparation of zeolite A is described in U.S. Pat. No. 3,882,243. The structure, chemistry and use of natural and synthetic zeolites is presented in "Zeolite Molecular Sieves", D. W. Breck (John Wiley & Sons, New York, 1974).

CATALYST PREPARATION

As illustrated more particularly in the Examples, the invention catalyst can be prepared conveniently by slurrying an appropriate quantity of commercial non-acidic zeolite in an aqueous solution of a water-soluble or partially water-soluble compound of palladium. The pH of the slurry is adjusted into the alkaline range, and the slurry is stirred with mild heating for a period up to about one hour. The catalyst precursor solids are drained, and oven dried at a temperature above about 100° C.

The dried catalyst precursor solids are then calcined in air (i.e., molecular oxygen) at a temperature between about 400°–600° C. for a period between about 0.5–10 hours. The weight percent of palladium in the catalyst composition can vary in the range between about 0.1–5, based on the composition weight.

It is an essential feature of the present invention catalyst preparation that the calcination of the catalyst in the presence of molecular oxygen must be followed by calcination of the catalyst in a hydrogen or $C_1$–$C_{10}$ nonaromatic hydrocarbon-containing atmosphere. Illustrative of suitable $C_1$–$C_{10}$ nonaromatic hydrocarbons are alkanes such as ethane, propane, butane, isobutane, pentane, hexane, cyclohexane, octane, decane, and the like. The said hydrocarbons can contain heteroatoms such as oxygen, nitrogen and halogen which are non-interfering under the calcination conditions. Although not preferred, an aromatic-substituted alkane can also be employed, e.g., ethylbenzene.

The said essential calcination of the catalyst in a hydrogen or nonaromatic hydrocarbon atmosphere is conducted at a temperature between about 450°–600° C. for a period between about 0.5–10 hours.

The resultant calcined catalyst matrix can be formed into the shape of granules, pellets, extrudate, powders, tablets, fibers, or other such convenient physical structure.

If the sequence of calcination steps described above is not performed, then the catalyst that is obtained is not in accordance with the practice of the present invention. As indicated in the Examples, such a nonconforming catalyst tends to exhibit less reactivity and selectivity, and further, the said catalyst tends to have a shorter period of sustained activity in a continuous processing system for vinylcyclohexene conversion to ethylbenzene.

VINYLCYCLOHEXENE CONVERSION

Suitable reactors for the vapor phase conversion of vinylcyclohexene include either fixed bed or fluid bed reactors which contain the palladium or non-acidic zeolite carrier catalyst component. The gas fed to the reactors comprises vinylcyclohexene and molecular oxygen to which nitrogen, carbon dioxide, steam or the like may optionally be added as an inert diluent. Any vinylcyclohexene feed which remains unreacted can be recycled in the process if desired.

The oxidative dehydrogenation reaction is conducted at a temperature in the range between about 190°–260° C., and preferably at a temperature of about 200°–240° C. The pressure can vary in the range between about 1–200 psi.

In a continuous process, the residence time (i.e., catalyst contact time) of the feed stream normally will be in the range between about 0.5 and 20 seconds, and preferably in the range between about 1 and 15 seconds. Residence time refers to the contact time adjusted to 25° C. and atmospheric pressure. The contact time is calculated by dividing the volume of the catalyst bed (including voids) by the volume per unit time flow rate of the feed stream at NTP.

In terms of liquid hourly space velocity (LHSV), the flow rate of the vinylcyclohexene nominally will be in the range between about 0.5–5 v/v/hr.

In the present invention process, the optimal conversion and selectivity of vinylcyclohexene to ethylbenzene is achieved if the molar ratio of vinylcyclohexene to oxygen is in the range between about 1–5:1. If the said molar ratio shifts to values below 1:1 (i.e., less vinylcyclohexene), then there is an increase in the quantity of styrene produced. A greater proportion of oxygen appears to suppress hydrogenation of styrene to ethylbenzene.

It is not necessary to use pure oxygen as the source of oxygen. Air is a suitable source of oxygen and is desirable for reasons of economy. Alternatively, the oxidizing agent can be ozone (under conditions which prevent direct interaction of ozone and olefin) or a compound which can generate oxygen under reaction conditions (e.g., peroxides and hydroperoxides), or it can be a compound which contains an active-oxygen functional group (e.g., nitro derivatives). Aliphatic and aromatic nitro compounds which have a boiling point below about 250° C. are particularly useful as an oxidizing agent in place of molecular oxygen in the invention process. Thus, in another embodiment this invention provides a process for the production of ethylbenzene and aniline which comprises contacting vinylcyclohexene with a present invention palladium on non-acidic zeolite catalyst in the presence of nitrobenzene at a temperature between about 200° C. and 500° C. and a pressure between about 1 and 200 psi to yield ethylbenzene and aniline product.

The following examples are further illustrative of the present invention. The reactants and other specific ingredients are presented as being typical, and various modifications can be derived in view of the foregoing disclosure within the scope of the invention.

EXAMPLE I

This Example illustrates the preparation of a palladium catalyst, and the selective conversion of vinylcyclohexene (VCH) to ethylbenzene in accordance with the present invention.

A slurry admixture is prepared employing 10% palladium chloride ($PdCl_2$, 5 grams), Linde 3A zeolite (88 grams) and water (100 grams). The pH of the slurry admixture is adjusted to 8–10 with ammonium hydroxide, and the admixture is heated for 15–20 minutes with stirring. The catalyst precursor solids are recovered, washed with water, dried for 18 hours at 110° C., and calcined in air at 500° C. for 4 hours. The catalyst is then calcined in a propane atmosphere at 550° C. for one hour.

The recovered catalyst is crushed and sieved to yield 20–30 mesh catalyst particles. About 15 $cm^3$ of the catalyst composition is charged to a 7 mm I.D. glass tube reactor.

Vinylcyclohexene is contacted with the catalyst in the reactor under the conditions and with the results indicated in Table I.

As illustrated in Table I, the vinylcyclohexene conversion rate decreases slightly as the LHSV is increased, and the selectivity to ethylbenzene decreases in favor of styrene.

Other related experiments indicate that if the reaction temperature is lowered much below 200° C. (e.g., 143° C.), the vinylcyclohexene conversion rate drops off rapidly. Also, as the molecular oxygen content of the feedstream is increased, the conversion rate decreases to some degree and the yield of styrene increases.

TABLE I

| Run | Temp. (°C.) | LHSV[1] | VCH/ $O_2$[2] | VCH Conv. (wt %) | Selectivities (wt %) | | | |
|---|---|---|---|---|---|---|---|---|
| | | | | | VCH Ty[3] | EB[4] | Sty[5] | Unk[6] |
| 1 | 195 | 1 | 1 | 98.3 | 2 | 98 | tr | tr |
| 2 | 210 | 1 | 1 | 99.6 | 1 | 99 | tr | tr |
| 3 | 225 | 2 | 1 | 91.9 | 2 | 95 | 3 | — |
| 4 | 230 | 2 | 1 | 81.5 | 1 | 87 | 12 | tr |
| 5 | 210 | 3 | 1 | 78.7 | 2 | 87 | 11 | tr |
| 6 | 220 | 4 | 1 | 51.1 | 5 | 58 | 37 | tr |
| 7 | 200 | 1 | 1 | 99.7 | 2 | 97 | 1 | tr |
| 8 | 210 | 2 | 1 | 86.5 | 1 | 83 | 16 | tr |
| 9 | 205 | 3 | 1 | 91.3 | 2 | 93 | 5 | tr |
| 10 | 211 | 4 | 1 | 66.8 | 2 | 73 | 25 | tr |

[1] LHSV = Liquid Hour Space Velocity of VCH
[2] Mole Ratio
[3] VCH Ty = Components Related to VCH Such as Ethylcyclohexene, but not VCH
[4] Ethylbenzene
[5] Styrene
[6] Unk = Unknowns, species heavier than styrene. In most cases this consists mainly of acetophenone.

EXAMPLE II

This Example illustrates the preparation of a catalyst and the conversion of vinylcyclohexene to ethylbenzene and other products in a manner similar to that described in Example I, with the exception that the palladium on non-acidic zeolite catalyst is not calcined in a propane atmosphere during its preparation.

The results of the vinylcyclohexene conversion are indicated in Table II. In comparison to the data reported in Table I, the data in Table II indicate that a palladium on non-acidic zeolite catalyst which is not calcined in a propane type atmosphere during preparation has poor activity for vinylcyclohexene conversion. The catalyst activity begins at a high level, and then drops off rapidly. The said catalyst has poor selectivity to either ethylbenzene or styrene.

TABLE II

| Run | Temp. (°C.) | LHSV | VCH/ $O_2$ | VCH Conv. (wt %) | Selectivities (wt %) | | | |
|---|---|---|---|---|---|---|---|---|
| | | | | | VCH Ty | EB | STY | Unk |
| 11 | 280 | 1 | 1 | 55.1 | 7 | 90 | 1 | 2 |
| 12 | 288 | 1 | 1 | 2.8 | 11 | 12 | 5 | 72 |
| 13 | 287 | 1 | 1 | 2.7 | 19 | 11 | 4 | 66 |
| 14 | 287 | 1 | 1 | 2.5 | 16 | 11 | 4 | 69 |
| 15 | 226 | 1 | 1 | 1.3 | 9 | 57 | 8 | 26 |
| 16 | 200 | 1 | 1 | 0.6 | 17 | 67 | 7 | 9 |
| 17 | 210 | 1 | 1 | 0.4 | 25 | 75 | 0 | tr |
| 18 | 208 | 1 | 1 | 0.4 | 40 | 60 | 0 | tr |

What is claimed is:

1. A process for converting vinylcyclohexene to ethylbenzene with a conversion of at least about 90 percent and a selectivity of at least about 95 percent, which comprises contacting the vinylcyclohexene with molecular oxygen at a temperature in the range between about 190°–260° C. in the presence of a catalyst consisting essentially of palladium supported on a non-acidic zeolite carrier substrate; wherein the said catalyst has been pretreated by calcination in a molecular oxygen-containing atmosphere and then by calcination in a hydrogen or $C_1$–$C_{10}$ nonaromatic hydrocarbon-containing atmosphere prior to vinylcyclohexene conversion.

2. A process in accordance with claim 1 wherein the conversion of vinylcyclohexene is at least 95 percent, and the selectivity to ethylbenzene is at least 98 percent.

3. A process in accordance with claim 1 wherein the molar ratio of vinylcyclohexene to oxygen is in the range between about 1–5:1.

4. A process in accordance with claim 1 wherein the liquid hourly space velocity (LHSV) of the vinylcyclohexene is in the range between about 0.5–5 v/v/hr.

5. A process in accordance with claim 1 wherein the carrier substrate is a non-acidic zeolite having a pore size which is less than about 5 angstrom units.

6. A process in accordance with claim 1 wherein the carrier substrate is zeolite A.

7. A process in accordance with claim 1 wherein the catalyst is pretreated by calcination in air at a temperature between about 400°–600° C., and then by calcination in a $C_1$–$C_{10}$ nonaromatic hydrocarbon atmosphere at a temperature between about 450°–600° C.

* * * * *